(12) United States Patent
Zhao et al.

(10) Patent No.: US 10,463,614 B2
(45) Date of Patent: Nov. 5, 2019

(54) BUTYLPHTHALIDE INTRAVENOUS EMULSION AND APPLICATION THEREOF

(75) Inventors: Chunshun Zhao, Guangzhou (CN); Zhanqi Niu, Shijiazhuang (CN); Zhen Chen, Shijiazhuang (CN); Haibo Guo, Shijiazhuang (CN)

(73) Assignee: SHIJIAZHUANG PHARMA GROUP NBP PHARMACEUTICAL CO., Hebei (CN)

( * ) Notice: Subject to any disclaimer, the term of this patent is extended or adjusted under 35 U.S.C. 154(b) by 26 days.

(21) Appl. No.: 13/112,180

(22) Filed: May 20, 2011

(65) Prior Publication Data

US 2011/0288167 A1 Nov. 24, 2011

Related U.S. Application Data

(63) Continuation of application No. 12/086,665, filed as application No. PCT/CN2006/003434 on Dec. 15, 2006, now abandoned.

(30) Foreign Application Priority Data

Dec. 16, 2005 (CN) .......................... 2005 1 0102355

(51) Int. Cl.
  *A61K 9/107* (2006.01)
  *A61K 9/00* (2006.01)
  *A61K 31/365* (2006.01)

(52) U.S. Cl.
  CPC ............ *A61K 9/107* (2013.01); *A61K 9/0019* (2013.01); *A61K 31/365* (2013.01)

(58) Field of Classification Search
  None
  See application file for complete search history.

(56) References Cited

U.S. PATENT DOCUMENTS

| 4,647,586 | A | * | 3/1987 | Mizushima et al. ........ 514/532 |
| 5,364,632 | A | * | 11/1994 | Benita et al. ................ 424/450 |
| 5,496,818 | A | * | 3/1996 | Schaupp ............ A61K 9/1075 514/224.8 |
| 2006/0166931 | A1 | | 7/2006 | Niu et al. |
| 2007/0167516 | A1 | | 7/2007 | Liu et al. |
| 2007/0265336 | A1 | * | 11/2007 | Feng et al. .................... 514/470 |

FOREIGN PATENT DOCUMENTS

| CA | 2 549 931 | 4/2005 |
| CN | 1 100 097 | 3/1995 |
| CN | 1 029 293 | 7/1995 |
| CN | 1 048 458 | 1/2000 |
| CN | 1 257 706 | 6/2000 |
| CN | 1 375 288 | 10/2002 |
| CN | 1 493 289 | 5/2004 |
| CN | 1 605 336 | 4/2005 |
| CN | 1 615 938 | 5/2005 |
| CN | 1 647 796 | 8/2005 |
| EP | 1 679 070 | 7/2006 |
| EP | 1 709 962 | 10/2006 |
| EP | 1 757 286 | 2/2007 |
| EP | 1 787 638 | 5/2007 |
| JP | 01-226807 | 9/1989 |
| JP | 2000-128786 | 5/2000 |
| JP | 2003-277281 | 10/2003 |
| WO | WO 2004/018444 | 3/2000 |
| WO | 2004018444 | 3/2004 |
| WO | WO 2005/002568 | 1/2005 |
| WO | WO 2005/016308 | 2/2005 |
| WO | 2005072725 | 8/2005 |
| WO | WO 2005/072725 | 8/2005 |

OTHER PUBLICATIONS

Strickley (Pharmaceutical Research, 21(2): 201-230, 2004).*
PDF copy regarding predicted properties of butylphthalide (2015).*
Webpage: https://chem.libretexts.org/Core/Physical_and_Theoretical_Chemistry/Acids_and_Bases/Acid/Bronsted_Concept_of_Acids_and_Bases, May 2016.*
Japanese Notice of Reasons for Rejection, dated Oct. 4, 2011, issued in corresponding Japanese Patent Application No. 2008-544744.
European Office Action, dated Aug. 10, 2011, issued in corresponding European Patent Application No. 06828348.0.
Z. Chong, et al., "dl-3-n-butylphthalide reduces brain damage in mice with closed head injury," Chinese Medical Journal 113(7): 613-616 (2000).
Written Opinion, dated Feb. 22, 2007, issued in corresponding International Application No. PCT/CN2006/003434.
International Search Report, dated Feb. 22, 2007, issued in corresponding International Application No. PCT/CN2006/003434.
International Preliminary Report on Patentability, dated Feb. 15, 2008, issued in corresponding International Application No. PCT/CN2006/003434.
European Search Report, dated Nov. 5, 2009, issued in corresponding European Patent Application No. 06828348.0.
Q. Chang, et al., "Effects of chiral 3-n-butylphthalide on apoptosis induced by transient focal cerebral ischemia in rats," Acta Pharmacol Sin 24(8): 796-804 (2003).
Canadian First Office Action, dated Mar. 24, 2010, issued in corresponding Canadian Patent Application No. 2,633,170.
Chinese First Office Action, dated Feb. 16, 2007, issued in corresponding Chinese Patent Application No. 200510102355.2.

* cited by examiner

*Primary Examiner* — Bong-Sook Baek
(74) *Attorney, Agent, or Firm* — Hunton Andrews Kurth LLP

(57) ABSTRACT

The present invention discloses a butylphthalide intravenous emulsion for intravenous injection or infusion, containing butylphthalide or derivatives thereof as an active ingredient in an amount of 0.01~50 wt % and an excipient in an amount of 50~99.99 wt %, based on the total weight of the emulsion.

3 Claims, No Drawings

BUTYLPHTHALIDE INTRAVENOUS EMULSION AND APPLICATION THEREOF

CROSS-REFERENCE TO RELATED APPLICATIONS

This application is a continuation application of U.S. application Ser. No. 12/086,665, filed Jun. 16, 2008, now abandoned which claims priority to PCT International Application No. PCT/CN2006/003434, filed on Dec. 15, 2006, which claims priority to Chinese Patent Application No. 200510102355.2, filed on Dec. 16, 2005, hereby incorporated by reference.

FIELD OF INVENTION

The present invention relates to a butylphthalide preparation, and specifically to a butylphthalide intravenous emulsion and application thereof.

BACKGROUND OF THE INVENTION dl-3-n-Butylphthalide (NBP) also called butylphthalide is dl-3-butylisobenzofuran-1(3H)-one, which is a raceme. l-3-n-Butylphthalid is extracted from celery seeds. NBP acts on multiple steps of cerebral ischemia procedure, such as reducing infarct area after focal cerebral ischemia, increasing cerebral blood flow in ischemic area and improving microcirculation in cerebral ischemic area, protecting mitochondrial function, alleviating damage to nerve function, and improving cerebral energy metabolism after total cerebral ischemia. Chinese Patent Nos. 98125618.X, 03137457.3, 200310100222.2 and 200410001748.X respectively disclose the applications of butylphthalide in anti-thrombus and anti-platelet aggregation, the application of 1-n-butylphthalide in prevention and treatment of dementia, cerebral infarction and in manufacture of medicaments for treatment of cerebral ischemia.

Currently butylphthalide preparations available in market are only soft capsules. Since butylphthalide is of an oily liquid form, it can be dissolved in an oil phase or directly processed to form an emulsion, then can be packaged in hard capsules or soft capsules, or can be orally administered directly. However, butylphthalide has a relatively apparent first pass effect which leads to a relatively low bioavailability. In addition, cerebral ischemia patients usually are companied with dysphagia or coma, so that capsules cannot meet the clinical requirements for these patients. For cerebral ischemia patients, time is life. Therefore, it is vital to develop a new delivery system suitable for clinical application.

SUMMARY OF THE INVENTION

Since butylphthalide is an oily liquid and hardly dissoluble in water, a specific manufacture technology is employed in the present invention to process butylphthalide into an emulsion for intravenous administration. The butylphthalide intravenous emulsion of the present invention has the following advantages: the drug directly enters into systemic circulation, thus resulting in quick action; the solubility of butylphthalide is improved, resulting in a reduced dosage; and/or the targeting of butylphthalide to brain tissue is improved, thus reducing its toxic side-effects.

The emulsion of the present invention has a particle size of between 10 and 2000 nm, and may be administered via intravenous injection or infusion in order to achieve quick action and brain targeting effect.

The butylphthalide intravenous emulsion of the present invention comprises butylphthalide or derivatives thereof as an active ingredient in an amount of 0.01~50 wt %, preferably 0.01~20 wt %, more preferably 0.01~10 wt %, and an excipient in an amount of 50~99.99 wt %, preferably 80~99.9 wt %, more preferably 90~99.5%, based on the total weight of the emulsion. The excipient comprises an oil phase, an aqueous phase, an emulsifier, a stabilizer and/or an osmoregulation agent. Butylphthalide or derivatives thereof may be either a raceme of butylphthalide or derivatives thereof, or l-butylphthalide or derivatives thereof.

The excipient may comprise an oil phase in an amount of 0~50 wt %, preferably 0.1~40 wt %, an aqueous phase in an amount of 50~98 wt %, preferably 60~97 wt %, an emulsifier in an amount of 0.01~50 wt %, preferably 0.5~10 wt %, a stabilizer in an amount of 0~50 wt %, preferably 0~15 wt %, and an osmoregulation agent in an amount of 0~10 wt %, all based on the total weight of the excipient.

The process for manufacture of the butylphthalide intravenous emulsion of the present invention comprises the steps of, such as preparing a primary emulsion, homogenizing, sterilizing and quality controlling. The step of preparing the primary emulsion is carried out by utilizing ultrasonic method or high-speed shearing method (FA25 Model High Shear Emulsifying Machine, FLUKO Equipment Shanghai Co., Ltd.).

The step of homogenizing is carried out by utilizing a two-stage high pressure emulsifying and homogenizing method (Niro-Soavi NS1001L Model High Pressure Homogenizer and Avestin EmulsiFlex-C5 High Pressure Homogenizer) or microfluidizing technology. The step of sterilizing is carried out by using high pressure sterilizing under rotation. The quality controlling is mainly carried out by measuring particle size.

DETAILED DESCRIPTION OF THE INVENTION (1) Selection of Oil Phase

In the emulsion of the present invention, the oil phase generally has an amount in mass of 0~50% (w/v). It is required in the present invention that a therapeutically effective amount of drug should be dissolved in a relatively small amount of oil phase, no drug precipitate occurs or no layer separation occurs under cryogenic storage condition, and in the meantime a stable emulsion is able to be formed with an aqueous phase in the presence of an emulsifier. The oil phase as used in the present invention may be a natural vegetable oil with long chain fatty acid ester groups or a vegetable oil or fatty acid ester being subjected to structure modification and hydrolysis. The examples of those may be one of or a mixture of soybean oil (especially in injection grade), castor oil, tea-seed oil, peanut oil, cottonseed oil, sesame oil, rape oil, safflower oil, olive oil, coconut oil, palm oil and cacao oil; or may be a glyceride with a chain length of $C_6$~$C_{12}$ fatty acid, such as but not limited to Arlacel 80, Arlacel 86, Capmul MCM, Captex 200 (oil), Captex 355 (oil), Miglyol 812 (oil), Myvacet (oil), Myverol 18-92, glyceride oleate, glyceride linoleate, macrogol glyceryl laurate, ethyl oleate, ethyl linoleate, caprylocaproyl triglyceride, and a mixture thereof; or may be a mixture of the above long chain fatty acid esters and medium-chain fatty acid esters.

During the manufacture of an injection emulsion, a preferred oil phase has relatively little haemolysis effect and is refined. Besides generally used vegetable oils, the following oils may also be used in the present invention:

| | |
|---|---|
| Arlacel 80 (HLB = 4.3) | Sorbitan monooleate |
| Arlacel 86 (HLB = 2.8) | Glyceride oleate:propylene glycol (90:10) |
| Capmul MCM (HLB = 5.5~6.0) | Coconut oil C8/C10 monoglyceride or diglyceride |
| Captex 200 (oil) | Coconut oil C8/C10 propylene glycol diester |
| Captex 355 (oil) | Coconut oil C8/C10 triglyceride |
| Miglyol 812 (oil) | Coconut oil C8/C10 triglyceride |
| Myvacet (oil) | Purified and acetylated monoglyceride |
| Myverol 18-92 (HLB-3~7) | Purified sunflower oil monoglyceride (containing 90% of glyceride linoleate) |
| Peceol (HLB = 3) | Glyceride oleate |
| Maisine (HLB = 3) | Glyceride linoleate |
| Gelucire 44/14 (HLB = 14) | Macrogol glyceryl laurate |

(2) Selection of Emulsifier

The emulsifier as used in the present invention may be one of or a mixture of nonionic surfactants and anionic surfactants. The preferred emulsifier may be but not limited to one of or a mixture of soybean lecithin or modified soybean lecthin (natural or synthesized), ovolecithin or modified ovolecithin (natural or synthesized), Ophase 31, Poloxamer 108, Poloxamer 188, Poloxamer 407, polyoxyethylene (hydrogenated) castor oil, water soluble VE (TPGS), Solutol HS-15, PEG-400 monostearate, PEG-1750 monostearate, Tween-80, Tween-20, and Span-20. It is preferred to use a mixture of these emulsifiers. During the manufacture of an injection emulsion, the preferred emulsifier has relatively little haemolysis effect and is refined. Besides the above emulsifiers, the following may also be used in the butylphthalide emulsion of the present invention:

| | |
|---|---|
| Ophase 31 (HLB = 4) | Liquid lecithin |
| Soybean lecithin (HLB = 4/7/9) | Soybean lecithin |
| Cremophor EL (HLB = 13.5) | Polyoxyethylene castor oil |
| Poloxamer 108 (HLB = 30.5) | Polyoxyethylene polyoxypropylene ether F-38 |
| Poloxamer 188 (HLB = 29) | Polyoxyethylene polyoxypropylene ether F-68 |
| Poloxamer 407 (HLB = 21.5) | Polyoxyethylene polyoxypropylene ether F-127 |
| Tween 80 (HLB = 15) | Polyoxyethylene sorbitan monoleate |
| Tween 20 (HLB = 16.7) | Polyoxyethylene sorbitan monolaurate |
| Span 20 (HLB = 8.6) | Sorbitan monolaurate |

(3) Selection of Stabilizer

Suitable stabilizer as used in the present invention may be but not limited to one of or a mixture of oleic acid, sodium oleate, sodium caprylate, cholesterol, cholic acid, deoxycholic acid and sodium salt thereof, vitamin A, vitamin C, and vitamin E.

(4) Selection of Osmoregulation Agent

Suitable osmoregulation agent as used in the present invention may be but not limited to one of or a mixture of sodium chloride, glucose, sorbitol, xylitol, mannitol, and glycerol.

(5) Basic Formulation of Butylphthalide Intravenous Emulsion

In the butylphthalide intravenous emulsion of the present invention, the ratio of butylphthalide:oil phase:emulsifier:aqueous phase:stabilizer:osmoregulation agent is any ratio (by weight) within the range of 0.01~50 wt %:0~50 wt %:0.01~50 wt %:50~98 wt %:0~50 wt %:0~10 wt %.

In one embodiment, the butylphthalide intravenous emulsion of the present invention has the following composition:

| | |
|---|---|
| Butylphthalide | 10 g |
| Oil phase | 100 g |
| Emulsifier | 50 g |
| Stabilizer | 50 g |
| Aqueous phase | Added to 1000 ml |

DESCRIPTION OF THE PREFERRED EMBODIMENTS

EXAMPLE 1

Preparation of Butylphthalide Intravenous Emulsion

| Formula composition | (g) |
|---|---|
| Butylphthalide | 10 |
| Soybean lecithin | 12 |
| Soybean oil | 100 |
| Vitamin E | 1 |
| Sorbitol | 25 |
| Water for injection | Added to 1000 ml |

The preparation process comprises the steps of: butylphthalide, vitamin E and soybean oil were weighed and mixed to form an oil phase, and the oil phase was pre-heated in a 60° C. water bath. Soybean lecithin and sorbitol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 2

Preparation of Butylphthalide Intravenous Emulsion

| Formula composition | (g) |
|---|---|
| Butylphthalide | 15 |
| Castor oil | 100 |
| Soybean lecithin | 12 |
| Poloxamer 188 | 6 |
| Glycerol | 25 |
| Oleic acid | 10 |
| Water for injection | Added to 1000 ml |

The preparation process comprises the steps of: butylphthalide, soybean lecithin, oleic acid and castor oil were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 3

Preparation of Butylphthalide Intravenous Emulsion

| Formula composition | (g) |
|---|---|
| Butylphthalide | 20 |
| Soybean lecithin | 12 |
| Olive oil | 100 |
| Cholic acid | 1 |
| Mannitol | 20 |
| Water for injection | Added to 1000 ml |

The preparation process comprises the steps of: butylphthalide, cholic acid and olive oil were weighed and mixed to form an oil phase, and the oil phase was pre-heated in a 60° C. water bath. Soybean lecithin and mannitol were weighed and dispersed in water to form an aqueous phase, and the aqueous phase was pre-heated in a 60° C. water bath. The oil phase was slowly poured into the aqueous phase, and the mixture was treated with ultrasonic waves for 10 times (10 seconds for each time, power: 400 W). Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 4

Preparation of Butylphthalide Intravenous Emulsion

| Formula composition | (g) |
|---|---|
| Butylphthalide | 25 |
| Cottonseed oil | 100 |
| Ovolecithin | 12 |
| Poloxamer 188 | 20 |
| Glycerol | 25 |
| Sodium oleate | 10 |
| Water for injection | Added to 1000 ml |

The preparation process comprises the steps of: butylphthalide, ovolecithin, sodium oleate and cottonseed oil were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 5

Preparation of Butylphthalide Intravenous Emulsion

| Formula composition | (g) |
|---|---|
| Butylphthalide | 30 |
| Soybean lecithin | 12 |
| Soybean oil | 200 |
| Tween 80 | 6 |
| Vitamin E | 8 |
| Xylitol | 100 |
| Water for injection | Added to 1000 ml |

The preparation process comprises the steps of: butylphthalide, Tween 80, vitamin E and soybean oil were weighed and mixed to form an oil phase, and the oil phase was pre-heated in a 60° C. water bath. Soybean lecithin and xylitol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 6

Preparation of Butylphthalide Intravenous Emulsion

| Formula composition | (g) |
|---|---|
| Butylphthalide | 40 |
| Caprylocaproyl triglyceride | 200 |
| Soybean lecithin | 12 |
| Poloxamer 188 | 20 |
| Glycerol | 25 |
| Oleic acid | 10 |
| Water for injection | Added to 1000 ml |

The preparation process comprises the steps of: butylphthalide, soybean lecithin, oleic acid and caprylocaproyl triglyceride were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 7

Preparation of Butylphthalide Intravenous Emulsion

| Formula composition | (g) |
|---|---|
| Butylphthalide | 50 |
| Soybean lecithin | 15 |
| Sesame oil | 100 |
| Vitamin E | 8 |
| Glycerol | 22.5 |
| Water for injection | Added to 1000 ml |

The preparation process comprises the steps of: butylphthalide, vitamin E and sesame oil were weighed and mixed to form an oil phase, and the oil phase was pre-heated in a 60° C. water bath. Soybean lecithin and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 8

Preparation of Butylphthalide Intravenous Emulsion

| Formula composition | (g) |
|---|---|
| Butylphthalide | 20 |
| Soybean oil | 100 |
| Ovolecithin | 12 |
| Poloxamer 188 | 20 |
| Glycerol | 25 |
| Sodium oleate | 10 |
| Water for injection | Added to 1000 ml |

The preparation process comprises the steps of: butylphthalide, ovolecithin, sodium oleate and soybean oil were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 9

Preparation of Butylphthalide Intravenous Emulsion

| Formula composition | (g) |
|---|---|
| Butylphthalide | 100 |
| Ovolecithin | 20 |
| Poloxamer 188 | 20 |
| Glycerol | 25 |
| Sodium oleate | 30 |
| Water for injection | Added to 1000 ml |

The preparation process comprises the steps of: butylphthalide, ovolecithin and sodium oleate were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 10

Preparation of Butylphthalide Intravenous Emulsion

| Formula composition | (g) |
|---|---|
| Butylphthalide | 0.1 |
| Soybean oil | 100 |
| Ovolecithin | 19 |
| Poloxamer 188 | 25 |
| Glycerol | 25 |
| Water for injection | Added to 1000 ml |

The preparation process comprises the steps of: butylphthalide, ovolecithin and soybean oil were weighed and mixed to form an oil phase, and the oil phase was pre-heated in a 60° C. water bath. Poloxamer 188 and glycerol were weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

EXAMPLE 11

Preparation of Butylphthalide Intravenous Emulsion

| Formula composition | (g) |
|---|---|
| Butylphthalide | 5 |
| Soybean oil | 100 |
| Ovolecithin | 12 |
| Poloxamer 188 | 20 |
| Sodium oleate | 3 |
| Water for injection | Added to 1000 ml |

The preparation process comprises the steps of: butylphthalide, ovolecithin, sodium oleate and soybean oil were weighed and mixed to form an oil phase, and the oil phase was pre-heated in a 60° C. water bath. Poloxamer 188 was weighed and dispersed in water to form an aqueous phase, and the aqueous phase was pre-heated in a 60° C. water bath. The oil phase was slowly poured into the aqueous phase, and the mixture was dispersed by using a high shear emulsifying machine under 10,000 rpm for 5 min. Then the mixture was circulated in a high pressure homogenizer for 5 times, in which the first stage pressure is 100 MPa and the second stage pressure is 10 MPa. Then the emulsion was regulated to have a pH of 8, filtered, subpackaged and sterilized at 121° C. for 15 min. Nitrogen gas is fed for protection during the whole process.

We claim:

1. A butylphthalide intravenous emulsion, consisting of following components by weight: 100 parts of butylphthalide, 20 parts of ovolecithin, 20 parts of Poloxamer 188, 25 parts of glycerol, 30 parts of sodium oleate and water for injection balanced to 1000 parts in total.

2. The butylphthalide intravenous emulsion according to claim 1, wherein the butylphthalide is a racemate of butylphthalide or l-butylphthalide.

3. The butylphthalide intravenous emulsion according to claim 1, which is in a form for intravenous injection or infusion.

* * * * *